(12) United States Patent
Kruger (10) Patent No.: US 10,548,511 B2
(45) Date of Patent: Feb. 4, 2020

(54) WEARABLE BODY MONITORS AND SYSTEM FOR COLLECTING AND ANALYZING DATA AND AND PREDICTING THE TRAJECTORY OF AN OBJECT

(71) Applicant: Benjamin Douglas Kruger, Lexington, KY (US)

(72) Inventor: Benjamin Douglas Kruger, Lexington, KY (US)

( * ) Notice: Subject to any disclaimer, the term of this patent is extended or adjusted under 35 U.S.C. 154(b) by 226 days.

(21) Appl. No.: 15/473,125

(22) Filed: Mar. 29, 2017

(65) Prior Publication Data

US 2018/0311530 A1    Nov. 1, 2018

Related U.S. Application Data

(60) Provisional application No. 62/315,097, filed on Mar. 30, 2016.

(51) Int. Cl.
*A63B 24/00* (2006.01)
*A61B 5/11* (2006.01)

(52) U.S. Cl.
CPC ............ *A61B 5/11* (2013.01); *A63B 24/0006* (2013.01)

(58) Field of Classification Search
CPC ....................................................... A61B 5/11
See application file for complete search history.

(56) References Cited

U.S. PATENT DOCUMENTS

2015/0250420 A1* 9/2015 Longinotti-Buitoni ...................... A61B 5/6804
                                                                                              600/301
2016/0206242 A1* 7/2016 Esposito .............. A61B 5/1038

* cited by examiner

*Primary Examiner* — Jay Trent Liddle
*Assistant Examiner* — Alex F. R. P. Rada, II
(74) *Attorney, Agent, or Firm* — Michael Coblenz (57) ABSTRACT

A method of analyzing data obtained from sensors worn on the body of an athlete. The sensors provide both location and physiological data. The sensors provide data to a computer program that can analyze the movement of the athlete and compare it to prior movement or optimal movements. The computer program can determine better motions to optimize performance based on the motion data from the sensors. The program can also determine physiological changes for the athlete, such as for example increasing leg strength, to optimize the performance. The program can also analyze and predict the trajectory of the sports object based on the data obtained regarding the athlete's movements and capabilities.

1 Claim, 4 Drawing Sheets

WEARABLE BODY MONITORS AND SYSTEM FOR COLLECTING AND ANALYZING DATA AND AND PREDICTING THE TRAJECTORY OF AN OBJECT

CROSS REFERENCE TO RELATED APPLICATIONS

This application claims priority to U.S. provisional application Ser. No. 62/315,097, filed on Mar. 30, 2016, and incorporated herein by reference.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

Field of the Invention

This invention relates to a system and method of using body monitors on an athlete for analyzing and improving athletic performance, storing and analyzing the date obtained from the body monitors for producing bio-feedback and recording and analyzing body motion, and for predicting the ultimate trajectory of an object.

BACKGROUND OF THE INVENTION

The invention relates to methods and apparatus for sports training. In particular, a trajectory prediction, analysis and feedback system is provided for an object launched, impacted, or released by a human and provides feedback regarding the trajectory of the object.

Most standards of a player's success are determined upon their consistency of controlling the trajectory of the object used in the game. To truly become a better athlete, one must understand how each body part's motion is effecting the trajectory of the object, how each consistency of the body part's particular motion is affecting the trajectory of the object, and how physiological conditions are affecting the trajectory of the object.

Users use a variety of techniques to improve their performance. Practice, sport specific strength training, and sport specific diets are all very common. Throughout history, coaches have attempted to determine the best way to perform a specific athletic endeavor. Many coaches prefer a hands-on approach when analyzing a user's athletic performance. Many coaches use the so called "eye test", meaning they watch the motion, and provide feedback to the user. Coaches based their feedback on prior history and knowledge of watching different approaches that worked for different users. This method turns into trial and error and a lot of frustrating moments throughout the process. One disadvantage to this method is the amount of time it takes a human being to blink and the amount of time it takes an experienced user to complete a motion like a swing. These two can overlap and cause problems in the coaching process. Another disadvantage is coaches are unable able to accurately decipher the current physiological scenario of the user, including the amount of muscle fiber activation rates, amount of lactic acid, amount of fatigue, the current heart rate, and other variables which significantly affect the particular motion, and in turn the trajectory of the object. The last disadvantage of the eye test is the instructions can be "lost in translation". By attempting to show the user how to correctly preform the motion, the coaches motion will not be an exact replica of what the coach thinks the motion should be. There will be deviations in the process, which leads to confusion.

Other coaches use video cameras to record the user and show the user what they did wrong. The major disadvantage for this process is, even though we can repeatedly study the user's motion, the internal body features are unknown. We are still using the "eye test" based on other users' performances to better the user's motion.

Modern technology has vastly improved the ability to train a user to perfect the various aspects of his or her sport. It is common to video record users and allow them to see themselves in action. This allows the user and a coach to evaluate every aspect of the user's performance, from their fundamentals to their game related behavior. A basketball player can watch game tapes to see how they were shooting, and to evaluate, in slow motion, what they did wrong during a particular shot.

There are now numerous sensors that can be used to assist users. The most common and well known is the FitBit® which measures the number of steps a person takes, but can also measure heart rate, blood pressure and body temperature. All of that data can help a user and coach evaluate the user's performance. Another common technique is to apply video sensitive tape (or tight-fitting clothing with video sensitive reflectors) and video the user during simulated aspects of their sport—a golf swing, a pitcher throwing—and develop a computer model of the specific user's body movement. This can be done for every aspect of the particular user's sport. This allows the coach to evaluate the specific body movements for efficiency and maximum performance. Runners, for example, can determine the most effective leg movement to increase speed or endurance.

The exponential growth in technology provides new ways to analyze athletic performance. There are a number of different sensors that can be attached directly to the user's body, or equipment, to provide data on the user's movement during a specific athletic event, such as swinging a golf club. These sensors can be attached directly to the skin by use of tape. These sensors can also be attached to the clothing that the user wears. The three most common types of sensors are the inertial monitoring unit, the IMU, and the surface electromyography, or SEMG, monitors, and electrocardiogram, or EKG, monitors. The SEMG monitors muscle fibers, through surface electromyography SEMG. The EKG's main function is to monitor the said user's heart rate. The IMU monitors the said user's motion.

These sensors can provide a good deal of information about an user's body motion while performing an athletic task, like swinging a golf club, throwing a pitch, shooting a basket, and the like. This information can be used to help the user improve performance. It would be valuable to further analyze this data to help the user improve performance by incorporating strength training and diet.

SUMMARY OF THE INVENTION

This invention is the apparatus and methods to 805 predict the trajectory of an object in a real time after an 300 ergonomic or athletic motion is captured by 200 sensors. The 200 sensors 300 capture and 600 analyze the body movements of the user, as well as 600 specific the physiological conditions of the user's body, such as heart rate, muscle activation, and other electromagnetic activity results within the user's muscles and heart. The invention's 200 sensors are contained in 100 skin tight clothing worn by the user. The 200 sensors transmit information to a separate 203 preferred method, more specifically a computer, tablet, or cellular device. From which, the 300 data is sent to a 204 server which contains software that 400 records, 600 analyzes, 805 predicts the trajectory to a 300 specific motion, and 450 archives the data. Such 600 analyzed data is finally sent back to the 203 preferred method to 900 display the 805 results of the trajectory analysis and biofeedback pertaining the 805 trajectory analysis.

The 706 biofeedback, or optimal motion, provides information to the user to allow them to modify their 300 movements and obtain their 700 desired trajectory more consistently. This said 708 optimal motion is produced by combining different body part's motions from multiple 450 historical motions. The process also uses the 701 historical data to predict how the users' 706 trajectory can be improved by modifying their body through weight adjustment or strength training. The process is able to tell the said user, for example, the 707 exact amount of added performance if their right triceps brachii increased in strength by 7%, and to achieve this, the user should engage in a personalized strength training program. The process is also able to tell the user, based on 600 historical physiological data recorded from the specific user, that the advised strength training program will be most effective if the user modifies his or her diet.

The inventions process allows any user to teach their favorite training program, trick shot, athletic motion, workout program, ergonomic trade secret, or 300 any other motion. For this sequence to occur, the producer of the 300 motion would have to wear the 100 garment, 300 preform their motion, label the motion, and 450 archive the motion via their 203 preferred method. This 450 archived motion is then available to be viewed on any 900 system clients. This instantly connects the best coaches to predecessors all over the world.

The final inventions process uses 400 data and 600 analytics collected from said user's 300 motions for the purpose of programming a robotics unit. The robotics application allows every end user to 450 archive their 300 motions for the purpose of teaching a robot a new 300 motion/skill. The invention completes a similar process of 900 displaying the 708 ideal motion to achieve their 700 desired trajectory, but instead of 900 displaying the motion via an avatar, the 450 data and 600 analytics are downloaded to a robotics unit for the purpose of increasing a robots ability.

DESCRIPTION OF THE INVENTION

The invention uses 300 data collected through 200 sensors to calculate the specific 300 movement and 600 performance of an end user, to 805 predict the trajectory of an object. These 200 sensors include from 201 surface electromyography, also referred by SEMG sensors, 201 Electrocardiogram, also referred to by EKG, and 202 Inertial Measurement Units, also referred by IMU sensors, which are a combination of two or more of accelerometers, gyroscopes, magnetometers, and barometers. These 200 sensors are embedded in or are attachable to 100 clothing worn on the user's body. The 300 data is collected and sent wirelessly from a 202 microcontroller, which is attached to the 100 clothing, to a 203 preferred method, either a cellular device, tablet, or computer. The 300 data is then sent to a 204 server to be processed. Finally, the 300 data is sent back the 203 preferred method to be 900 displayed. The 204 server uses the 300 data collected to 805 predict the trajectory of an object given an athletic or ergonomic motions. The inventions process also uses the 805 trajectory results and 701 correlates the trajectory with each body parts 300 specific motion, each 300 specific muscles exact muscle fiber activation rate, the user's 300 heart rate, and their respective 600 analytics. Through the 701 correlation and 600 analytics, the process has the ability to introduce an 708 'optimal motion'. The 708 'optimal motion' is the exact ergonomic or athletic motion that will most consistently provided the user with their 700 desired trajectory.

Figure 1:
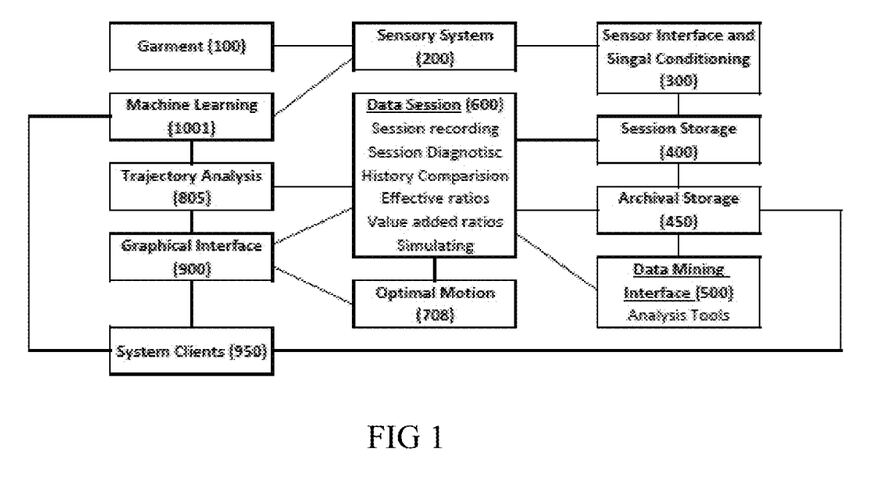
FIG. 1 is a flow chart of a method for using data collected from sensors for the purpose of predicting the trajectory of an object and providing bio feedback using a trajectory analysis and detection system
Figure 2:
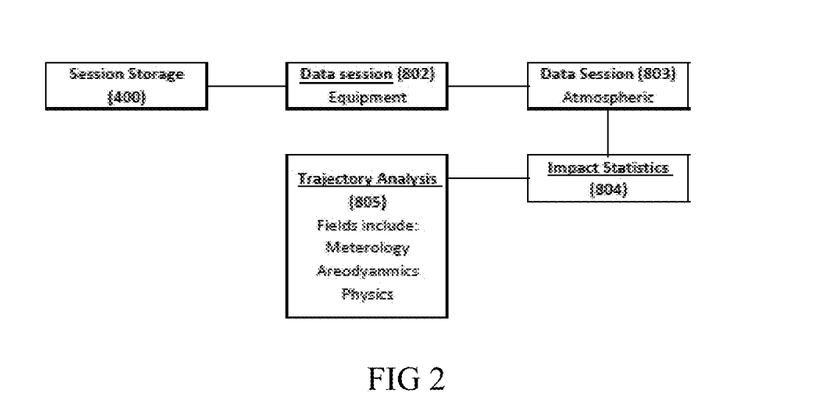
FIG. 2 is a flow chart of a method for trajectory prediction
Figure 3:
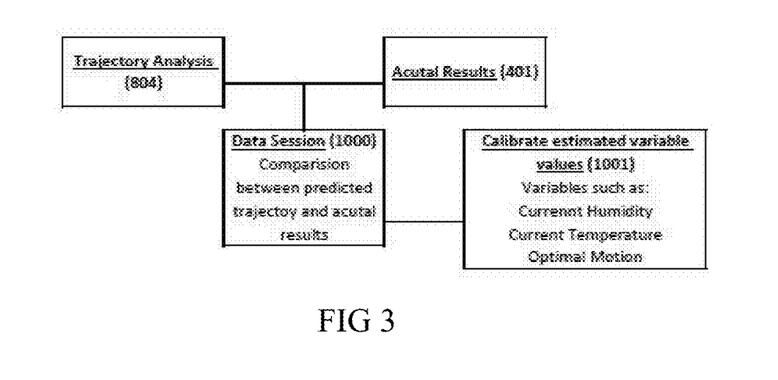
FIG. 3 is a flow chart of a method for producing an optimal motion during a trajectory analysis and detection system
Figure 4:
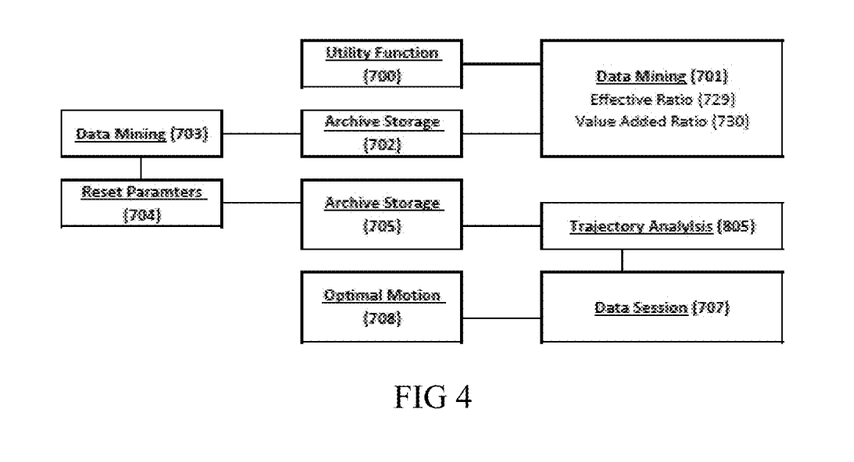
FIG. 4 is a flow chart of a method for machine learning during a trajectory analysis and detection system
Figure 5:
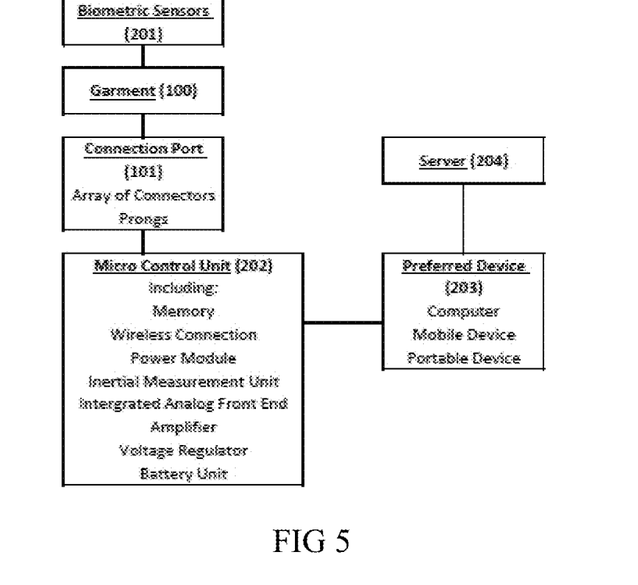
FIG. 5 is an information flow diagram for the apparatus of the invention during a trajectory analysis and detection system

FIG. 1 is a flow chart of a method for using data collected from sensors for the purpose of predicting the trajectory of an object and providing bio feedback using a trajectory analysis and detection system. FIG. 2, FIG. 3, FIG. 4, and FIG. 5 show more details of specific processes included in FIG. 1. FIG. 2 is a flow chart of a method for trajectory prediction and visually shows the steps for the prediction process. FIG. 3 is a flow chart of a method for producing an optimal motion by using the method of predicting a trajectory of an object. FIG. 4 is a flow chart of a method for machine learning during a trajectory analysis and detection system. This process is used when updating variables for the trajectory. It is also used when back testing the theoretical optimal motion against an actual motion. FIG. 5 is an information flow diagram for the apparatus of the invention during a trajectory analysis and detection system. This shows the connection between the sensors and the order the data is relayed.

Figure 6:
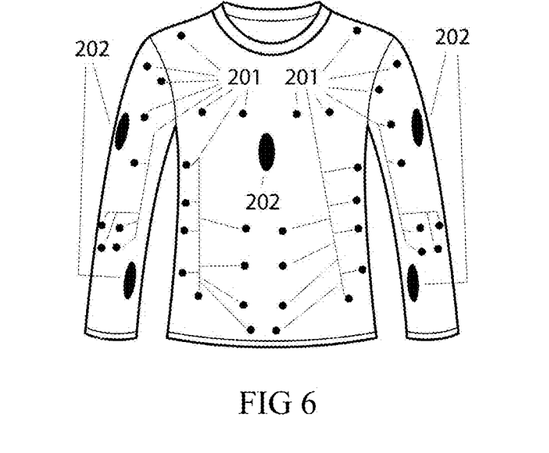
FIG. 6 shows the location of the 202 microcontroller (including the IMUs), and the 201 electrodes on the front of the 100 compression shirt
Figure 7:
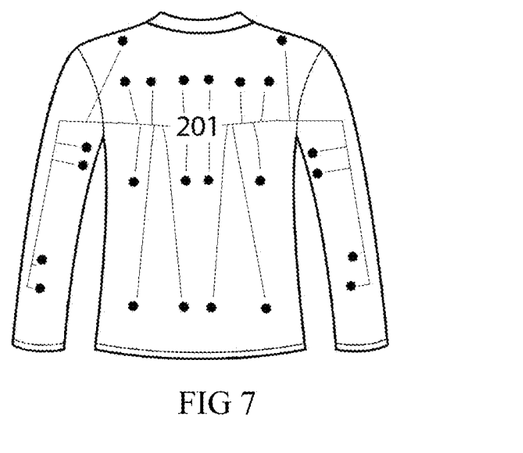
FIG. 7 shows the location of the 202 microcontroller (including the IMUs), and the 201 electrodes on the back of the 100 compression shirt
Figure 8:
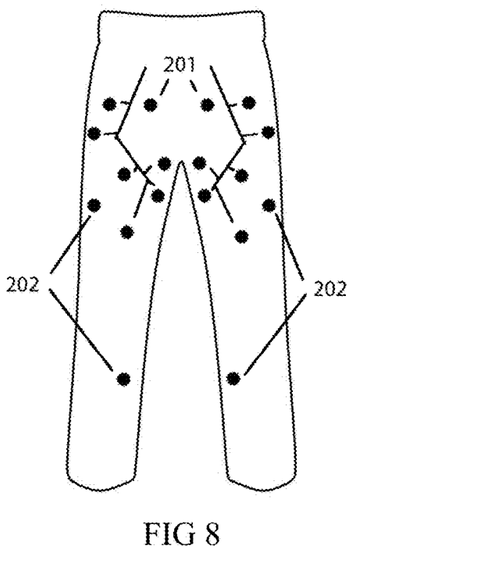
FIG. 8 shows the location of the 202 microcontroller (including the IMUs), and the 201 electrodes on the front of the 100 compression pants
Figure 9:
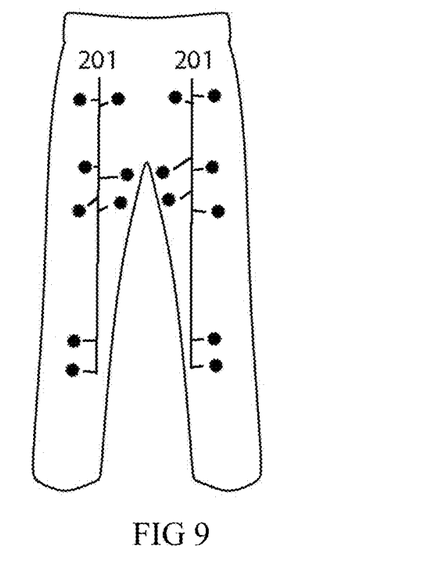
FIG. 9 shows the location of the 202 microcontroller (including the IMUs), and the 201 electrodes on the back of the 100 compression pants
Figure 10:
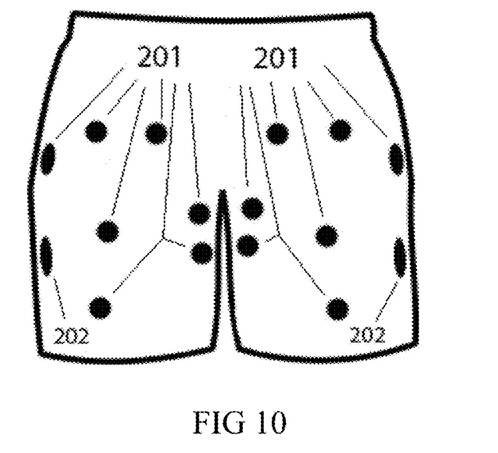
FIG. 10 shows the location of the 202 microcontroller (including the IMUs), and the electrodes on the front of the 100 compression shorts
Figure 11:
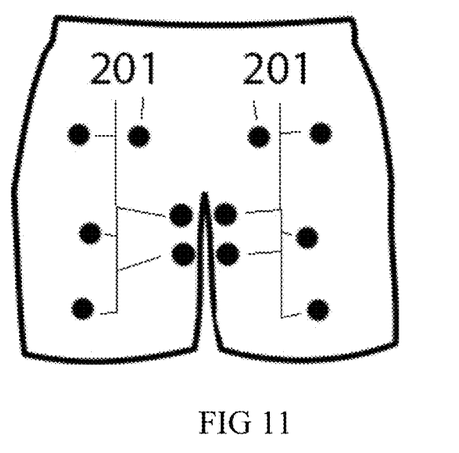
FIG. 11 shows the location of the 202 microcontroller (including the IMUs), and the 201 electrodes on the back of the 100 compression shorts

FIG. 6 and FIG. 7 show the location of the 200 sensors in the 100 shirt. The 201 sensors are electrodes used in the Surface Electromyography and Electrocardiography. The 202 sensors are attachable microcontrollers that consist of at least an inertial measurement unit, memory, Wireless Connection, Power Module, Integrated Analog Front End, Amplifier, and a Voltage Regulator. FIG. 8 and FIG. 9 show the location of the 200 sensors in the 100 compression pants. FIG. 10 and FIG. 11 show the location of the 200 sensors in the 100 compression shorts. There are two articles of 100 clothing, a shirt and compression pants, or compression shorts. The 100 clothing is skin tight to allow the 200 sensors to be directly against the user's skin. The 200 sensors can be incorporated into the clothing by sewing or other appropriate methods.

The location of each 202 IMU is also essential to this invention. FIG. 1 shows the locations of the 200 sensors on the 100 front of the shirt and shorts, while FIG. 2 shows the locations of the 200 sensors on the 100 back of the shirt and shorts. These locations were picked because they can 600 decipher the 300 exact motion for each and every body part and any given time. For example, the 202 IMUs on the shorts are able to tell the 600 amount of force and velocity of the feet, even though there are no 202 IMU's located on the feet, through a baseline system. The user's baseline coordinates are 0, 0, 0 when the user's joints are completely straight. The joints are completely straight when they are at the natural resting position. Using the baseline coordinates, the invention can process 600 deviations between repeated motions (including the set-up, the motion, and the completion of the motion), a most likely scenario of each body part throughout the motion, and the deviations effects on the motions results. Furthermore, the 200 sensors 600 calculate the angle of the ankle joints given their new coordinates.

For example, if the user's knees are at an angle of 180 degrees and there is vertical increase in the 100 compression shorts', or compression pants', 202 IMUs, we can 600 decipher that the user's feet raised by the exact vertical value. Another example explains how the invention's 202 IMU location can track sideways motion of the user's feet. By keeping their feet completely flat on the ground and maintaining a knee joint angle of 180 degrees, we can 600 decipher that any horizontal movement of the 202 IMUs is the direct result of in-toeing or out-toeing. Using the most likely scenario of motion (the motion and location of each and every body part) and the exact coordinates of the 202 IMU's, this invention archived the coordinates (on an x, y, z axis), rate of change (velocity), deviation between multiple motions when the user tries to produce the same motion (margin of error), amount of torque of each motion (risk of injury), among other 600 analytics throughout the entire 300 ergonomic or athletic motion.

The 202 IMU's are also responsible for 600 calculating the velocity and angular acceleration of the body parts. This is 600 calculated by the rate of x, y, z change given a time stamp. The 202 IMU's location can also provide the flexibility, range of motion, and other variables. The range of motion is all possible X,Y,Z values with respect to the other 202 IMU values. The other 202 IMU values are critical when calculating the range of motion to confirm the body is stagnate. Flexibility is the range of motion with respect to the 201 SEMG readings.

The IMU values of the most likely scenario are also 450 archived and a large standard deviation is applied to those values. This builds the frame work for an archived motion recognition process. The IMU ranges, or IMU values with the large standard deviation applied, are used to track when a motion occurs. More specifically, the IMU ranges, with respect to time t, create a data set, or parameters, to test every motion against. For example, a golf swing has a plane each IMU will follow. The plane will deviate throughout the round and will completely change over time, but the overall plane of the golfers swing will always be recognizable through the IMU ranges. When a motion is recognized, the archived data will be labeled for future data retrieval. Using the 600 analytics throughout the 300 motion, this invention claim's the ability to 805 predict the trajectory of a motion. For example, the 805 predictions include, but are not limited to, the flight of a golf ball, the motion of a kayak given the users paddle motion, and the risk of injury of an worker lifting a 50 pound box repeatedly. The invention continuously updates the repeated 300 motion's data and 600 develops analytics on the motion to inform and improve the user's 300 ergonomic and athletic motion.

The location of the 201 SEMG sensors allows the process to 300 monitor the muscle fiber activation rate for a select group of muscles. This is 600 measured by the electromagnetic activity in the muscles. The higher the activation rate, the more muscle contraction is evident. The invention also 600 monitors for the increase in the activation rate of muscle fibers that are not used to their full potential, which is different from muscle hypertrophy. Muscle hypertrophy by definition is the increase in size of skeletal muscle through a growth in size of its component cells. We will coin the term muscle hypertrophy for both scenarios, even though they have different meanings. The goal is to obtain a higher activation rate through added muscle fibers or tapping into dormant muscle fibers. This invention monitors and analyzes the changes in the activation rate of muscle fibers in the monitored muscles.

By monitoring the changes in muscle fiber activation rate, this invention also accurately 600 calculates the fatigue of each monitored muscle, amount of possible force per muscle, which muscles are stronger than others, which muscles are used most often during an ergonomic or athletic motion, which muscles contribute to the 805 trajectory of an object the most, and which muscles are more susceptible for muscle hypertrophy. A clear sign of fatigue is the decrease in activation rate for fast twitch muscle fibers. These muscle fibers produce a signal of 126-250 Hz. The amount of force per muscle is 600 calculated by dividing the newton's force by the cross-sectional area of the muscle. The amount force is than compared to all other muscles to decipher which muscles are stronger than the others. During a motion, the force divided by time t allows the process to decipher which muscles are most active. To tell the effects of fatigue for that particular user for the particular motion, the invention 600 calculates the deviations of the motion, using the 202 IMU data against the amount of fatigue. By comparing the fatigue of the specific muscles and their effect on the 805 trajectory, the process 600 deciphers how each body part reacts to fatigue and by a specific amount. Furthermore, we can provide training to reduce fatigue or a change in motion to compensate for fatigue. The training process minimizes the amount of fatigue given 450 historical data on how the specific user's muscles responded to a workout.

While lifting weights or performing an athletic motion, the 300 activation rate of muscle fibers can be a clear sign of many key 600 analytics including, but not limited to, the maximum amount of force, the maximum amount of force velocity, and the time until fatigue occurs for the specific muscle. Since muscle fibers are responsible for movement, the velocity and the force of the motion directly relate to the increase in muscle fibers. By using 450 historical data, the process can estimate the amount of changes in force, velocity, and flexibility during fatigue or if muscle hypertrophy occurred. The process uses a regression equation to estimate the added amount of max velocity with respect to the fast twitch and slow twitch muscle fibers. For example, the regression equations stipulates that the user, on average, will increase velocity by X and force by Y for each increase in muscle fibers. During a 300 motion, the 600 percent of activation for each muscle is a clear indicator which muscles are essential to the completion of the motion. If a lower than normal activation rate is noted, it can mean that there is wasted potential energy, but the process checks the increase in margin of error for each increase in muscle fiber activation for that muscle.

Similarly to the 201 SEMG, the 201 electrocardiogram, or EKG, measures the electromagnetic activity. Instead of measuring the electromagnetic activity of a muscle, the 201 EKG or ECG measures the electromagnetic activity of the heart. This data is used primarily for monitoring the heart rate of the user. Other analytics include the estimated respiration rate and monitor abnormalities. These abnormalities include heart attacks, a murmur, seizures, cardiac dysrhythmias, fainting, and other abnormalities. Even though the process searches for key signs in the abnormalities, the main purpose to monitor the heart rate through the ergonomic or athletic motion.

The 950 process begins with said user being instructed to complete a task, for example swinging a golf club at a number of different angles. (This description uses a golfer and a golf swing to illustrate how the invention works. However, the invention can be used with any sporting activity or ergonomic motion). The angles described in this section refer to the joint angles of the body. These angles are 600 measured by the timestamped 202 IMU sensors' baseline and most likely scenario process, which was briefly described above. The timestamped 202 IMU data is 600 analyzed and produces the velocity, margin of error, and amount of torque per body part while 300 performing the motion. The timestamped 201 SEMG data is also 300 collected and 600 analyzed, which shows how each 600 specific muscles are responding during the 300 motion, which was described above. By using the 201 SEMG sensors, the invention calculates the 600 exact amount of muscle fiber activation in each specific muscle monitored. The 300 SEMG data is then 600 indexed based on the number of muscle fibers activated, the maximum amount of muscle fibers produced, the average amount of force each muscle fiber produced, and amount of fatigue.

The invention uses a cause and effect method for 805 predicting the trajectory of an object. The cause is the 300 motion and 600 analytics the said user preforming the motion causes on the 805 object at the impact/release. Such 600 analytics include the amount of force caused to the object at impact, the velocity at impact, the angle of impact, and more. Also the "cause" aspect of the 805 trajectory analysis includes the 802 equipment variables such as the elasticity of the equipment, the center of gravity of equipment, the lead/lag of the equipment at impact, the mass of the equipment, the compressibility of the equipment, the friction of the equipment, the shape of the equipment, and more.

In more depth, the "cause" begins with using the 200 sensors to 600 calculate the 802 equipment variables with respect to time t. These analytics include the velocity of the equipment throughout the 300 motion, the elasticity of the equipment (e.g. the lead/lag of a golf club shaft throughout the swing), the aerodynamics, or external forces, on the equipment. The elasticity of the equipment refers to how the equipment responds to the motion. More specifically, how the motion creates a center of gravity that causes the equipment to bend. The elasticity of the equipment is also used to calculate the velocity of the equipment. For example, the golf shaft bends and "recoils" throughout the motion. The invention uses the elasticity of the equipment to accurately calculate the velocity of the club head and the location of the club head throughout the motion.

Once the location of the equipment at all times is calculated, the process calculates the impact statistics. These statistics include the impact velocity, the impact angular velocity, the impact angle, the compressibility of the equipment, the friction force, and the transfer of force. It also deciphers how the mass of the equipment and the mass of the object react with each other. The impact velocity is Impact Velocity=Displacement/time of impact. The friction force calculates how much energy is lost due to friction. The transfer of force measures how much force remains. These variables and analytics are then processed to predict the trajectory of the object.

Before the prediction of the trajectory is calculated, the process downloads, or estimates, the 803 atmospheric variables. Such 803 variables include the current gravity, wind, humidity, temperature, and the atmospheric pressures. After the 300 motion is completed and the 803 atmospheric variables are estimated, the process solves for the 804 launch angle produced with predicting analytics. Such 804 analytics include the amount of spin, direction of the spin, and more. With respect to the 803 atmospheric variables and 804 impact analytics, the 805 lift, drag, gravitational force, speed of the ball, linear acceleration, angular acceleration, landing velocity (vertical, horizontal, and depth), rebound velocity (or bounce), friction of ground impact, coefficient of restitution at rebound, and the spin are predicted. This 805 process gives the first predicted trajectory given the 803 estimates. This 805 process is then back tested and uses 1001 machine learning to reduce inaccuracies in the 805 prediction process.

There are three different variations of the 1001 machine learning process. The type of 1001 process used is dependent on the type of object and whether the object's 805 trajectory is being predicted until the final resting point or until a "moment of success" occurs. The type of object could be a baseball, basketball, or even said user's body (in the case of snowboarding and gymnastics). The difference between 805 predicting the trajectory until the final resting point and the "moment of success" is apparat when comparing golf and basketball. Once a basketball goes through the basketball goal, the 805 trajectory is irrelevant. On the other hand, a golf balls 805 trajectory is relevant until the final resting position.

The first 1001 variation is implemented when the 300 ergonomic or athletic motion requires 1001 predicting the trajectory for the entirety of the objects "momentum", or until the final resting position. To perform the 1001 machine learning system, the invention 1000 tests the 401 actual 
resting position against the 805 predicted results, and, if applicable, 1001 implements the machine learning process. The machine learning process is only applicable when the deviations between the actual and predicted statistics are significant. The 401 actual distance and location from impact can calculated through the 202 IMUs. For example, once the said user 300 completes a golf drive and 300 completes the fairway golf shot, the 202 IMU values for the time in between will 600 measure the 401 exact distance and location of the golf drive. The 401 real distance and locational value is then compared to the 805 predicted trajectory. If the 1000 standard deviation is in excess, a back test using 1001 machine learning will begin.

The second 1001 variation is implemented when the 300 ergonomic or athletic motion requires 850 predicting the trajectory until time t, or when the 850 trajectory is either successful or unsuccessful. The method requires a 300 "motion key" to signal to the 850 process if the object was successful. For example, every time a said user makes a 300 basketball shot without hitting the rim, a 300 specific "motion key" is implemented. In this example the said user's 300 motion key is pointing to the sky. If the 300 shot hits the backboard first and then is successful, the said user's 300 motion key is swiping his right hand left to right. If the 300 shot hits the rim first and then goes in, the said user 300 points down. This allows the process to 1000 back test the 850 trajectory for accuracy. For the basketball example, the 1001 process uses 1000 added variables, which include the basketball size and the basketball rim size, and the motion key to accurately solve for the 803 estimated atmospheric variables.

If the 300 ergonomic or athletic motion requires 805 predicting the trajectory of one such user, e.g. cheerleading or skiing, the 200 sensors will be used to back test the 805 predicted trajectory given the exact amount of muscle fiber activation rates in each muscle, launch angle and another relevant variables for the particular motion. In other words, the 805 prediction of the trajectory is instantly back tested against the 450 actual results. This 1001 process instantly calibrates the estimated variables for future 805 predictions of the trajectory. In practice, this 1001 calibration will be valuable if the user is considering a new 300 motion or how much the 803 weather conditions will factor into the implementation of the 300 motion.

If biofeedback and an 708 optimal motion is desired, the user will be introduced to the 700 'Utility Function'. The 700 'Utility Function' allows the user to customize their 850 trajectory to their 700 specific preferences, with respect to the specific 600 athlete's ability. This is the inventions way to decipher what the user values most and what percent more do they value it. Through this 700 process, all 450 historical data is collected and 701 analyzed as a whole with respect to the point of impact/release. This process runs a regression equation with variables consisting of accuracy, distance, risk of injury, and spin. It also runs a smoothed quintile model to find the estimated value for each variable at any percentage. These equations are the frame work for the initial toggles. For example, when distance goes up, accuracy goes down to the exact value quantified in the regression equation. This 702 framework is a simple estimation solely for the purpose of said user to understand what each 701 toggle does with respect to the said users desired 805 trajectory or tailored game. The said user can then make an educated decision on their gameplay preference.

The 708 process continues by analyzing 450 historical data of the said user. This 450 data pertains to each relevant ergonomic or athletic motion ever attempted by the said user. By 600 analyzing the data, the final product of a 708 customized motion based on the said users exact body is produced. To produce the customized, or 708 optimal motion, the process calculates two different perspectives of analytics. These perspectives, or statistical models, are coined the "effective ratios" and the "value added ratios".

701 "Effective ratios" are the metrics used to help explain how one moving body part effects the other body parts throughout the motion. To solve for the 701 effective ratios, the invention uses 450 historical data and runs statistical models with respect to each other body part, more specifically each 202 IMU. For example, the user's 600 standard deviation, velocity, acceleration, and time until fatigue said user's forearms are completely different if the users right quad moves left to right than if the right quad moves right to left during the motion. These metrics are with the respect to said user's physiological conditions when the motion occurred, such as heart rate, muscle fatigue, lactic acid, and stress levels. These effective ratios quantify the relationship between their moving parts given their physiological scenario.

Based on 450 historical data when attempting an exact motion repeatedly, the invention 600 calculates the said users' 600 analytics for each particular body part, or IMU, with respect to the motion's 805 trajectory. The process also factors all 450 historically experienced physiological conditions, such as the levels of fatigue, the different heart rates, the different levels of lactic acid, and their effect on the 300 motion, and in turn the 850 trajectory. This calculation is different from the said 701 effective ratios. As stated above, the 701 effective ratios calculate a body part's analytics with respect to the other body parts analytics. The 701 value added ratios calculate the analytics of each individual body parts with respect to the trajectory. In other words, the 701 value added ratios refers to how each body part's motion will affect the 805 trajectory of the object. An extremely inaccurate body part's 300 motion can consistently affect the 805 trajectory despite the other body part's remaining extremely consistent.

For example, the 703 process selected the right quad's motion with the 701 highest possible velocity. The 703 process simulates how much 701 added velocity that translate to the final impact velocity of the equipment, and in turn how much added value the motion adds to the 805 trajectory. Given the right quads' 450 historical data, the 701 expected standard deviation, average acceleration, average velocity we can expect a deviation in trajectory of 5 yards in any direction. This 701 deviation was more significant than the average. The 701 process quantifies an expected value added and expect margin of error for all body parts.

The final 708 process uses the 805 analyzed trajectory data, the 701 effective ratios, the 701 value added ratios, and the user's 700 utility function to produce a motion that matches the user's 700 desired trajectory. The 708 process begins by choosing an 202 IMU, such as the 202 IMU on the right quad, and selects the best motion given the 701 effective ratios and 701 added value ratios inside the 704 parameters. The 704 parameters consist of all possible motions which will give the user their 700 desired trajectory. The 704 process continues by narrowing the parameters for all other IMU's. For example, if the said user's right leg 300 pivots to the left during a baseball swing, the user's upper body 704 parameters would constrict. This constriction of 704 parameters compensates for the 300 unattended movements to the left caused by the 300 right quad motion. If this constriction of 704 parameters did not occur, the best statistical 708 motion for the forearms might lead to an 804 impact location on the tip of the bat instead of the face of the bat. Once the first 202 IMU's motion is 703 optimized and the 704 parameters are constricted, this 703 process is repeated for each 202 IMU until a 705 suggested optimal motion is completed. This 703 process is also repeated for every possible order of 202 IMU's. For example, then first order might be right quad, left quad, chest, left upper arm, left forearm arm, right upper arm, and then the right forearm. The next 703 data mining order will be right quad, chest, left quad, left upper arm, left forearm arm, right upper arm, and then the right forearm. Another order is chest, right quad, left quad, left upper arm, left forearm arm, right upper arm, and then the right forearm. From the list of 705 suggested optimal motions, the 701 added value ratios are applied and the 805 object trajectory is predicted given the law of large numbers. The 707 best possible motion is 450 archived and 900 displayed as the 708 optimal motion.

Another variation of this 708 process uses the 701 value added ratios in the 703 data mining process. This 703 process differs due to the fact that the 701 value added ratios are not the decider between 705 suggested optimal motions, but are used in the 703 data mining process. This 703 process uses the 701 effective ratios to set 704 parameters and give insight of which motion is better when considering the other 202 IMU's. The 701 value added ratios are used to maintain the 700 desired results throughout the 703 process and give insight of which motion is better when considering the 805 trajectory. In other words, the 701 added value ratios gives focus to the 703 process and is used to confirm the 700 desired results will be attained. For example, the user's right quad has a 701 large standard deviations with respect to the effective ratios, meaning other body parts are extremely correlated with the consistency of that particular motion. This 701 statistic, combined with a 701 large standard deviation when considering the 701 value added ratios, can lead to significant 850 trajectory deviations. But that motion also gives the best 707 possible results with respect to distance. This 708 process then compares this motions 705 statistical chance of maintaining the 700 desired trajectory consistently over time with another motion that has a 701 low standard deviation effective ratio but also has a 701 higher value added ratios. This trade off process is comparable to simple game theory. By the end of comparing each 202 IMU motion with other motions from the same IMU and with the other 202 IMU values, an 708 optimal motion with at least the values of the 700 utility function is produced. If multiple 705 motions produce similar results, the user's 700 preference on which analytics are valued the most is the determinant. For example, 10 705 suggested motions have the 700 statistics the said user desires. One has a much higher 805 expected accuracy while the other has a much higher 805 expected distance, and the user 700 values distance over accuracy. The 705 suggested optimal motion with the higher 805 expected distance will be 705 archived and 900 displayed on the 203 preferred device.

Both variations are 1001 back tested and some motions might not maintain their 701 statistics in the real long run. If another 705 suggested optimal motion's 805 trajectory is statistical significant when 1000 compared with the 401 actual motion, the suggested optimal motion will be 900 displayed to the user.

The invention uses a 900 visual approach to demonstrate the 708 optimal motion. The visual approach uses kinematics of rigid body to show the motion and analytics through a 3D avatar. 705 Each body parts motion, which was selected through its 701 analytics, is 900 displayed via the exact 708 IMU values at its respective time. By inserting each 708 IMU's values in the 900 avatars exact location with respect to time t, the 900 avatar produces an exact digital replica of its 708 optimal motion. The 708 optimal muscle fiber activation rates are then added to the 900 avatar with respect to time t. This 708 data is collected from the same location in which the 708 IMU's data was collected. 900 This shows the 708 optimal amount of flex for each muscle throughout the motion to give the 707 best results. It is 900 displayed through the avatars muscles, which are located in the respective locations, and gets darker when more muscle fiber activation occurs. As to say, the lighter colored muscles need less muscle fiber activation than the darker colored muscles.

After each 300 attempt of the 708 optimal motion, biofeedback is 900 displayed in three variations. For example, the 701 value added ratios determined user's 805 trajectory is 701 directly affected by the right quads motion by 10 yards southwest. So to say, the 701 deviations of the right quad was solely responsible for such quantified value of the 805 trajectory. If the right quad was directly consistent, the 805 trajectory would be normalized and the 701 10 yard southwest deviation would not have occurred.

One 900 variation of the bio feedbacks display is through a 900 qualitative display. The 900 qualitative display gives insight pertaining to the comparison of the 401 actual motion and the 708 optimal motion. The 1001 process continues by calculating the 701 effective and 701 value added ratios for each body part. After the 401 actual motion, the 900 qualitative display will choose the body part with the 701 highest correlation to the deviation of the 805 trajectory and give instructions like "Right quad was too far to the right at impact". 1001 This allows the user to adjust given the 900 qualitative instructions.

The second variation is through a 900 vocal announcement. The 900 vocal announcement, like the 900 verbal display, will 701 calculate the body part with the highest correlation to the deviation of the 805 trajectory. This 900 variation will announce instructions through the 203 preferred devices speaker like "Right quad was too far to the right at impact".

The third 900 variation is the 900 visual comparison biofeedback. 900 It will transparently overlay the 401 actual motion with the 708 optimal motion. 900 This shows not only the most 701 significant deviation from the 708 optimal motion, but every other 701 deviation from the 300 motion. 900 It allows for more advanced adjustments and demonstrations. This method 300 collects the data from the 200 sensors and 900 displays them through a kinematic of rigid body avatar, similar to the 708 optimal motion 900 display. The difference between the 708 optimal motion 900 display and the 401 actual motion 900 display is the collection of the data. Instead of using IMU data from 705 different historical motions, the IMU data displayed is from the 300 most recent recognized gesture motion.

If the said user is unable to obtain the 701 necessary analytics for their 700 desired results, or 805 trajectory, the invention has the ability to give a workout program and diet tailored to the said user's body makeup. The invention's process to produce the tailored training regimen is reliant on 300 IMU values, SEMG readings, EKG readings, and the 805 trajectory of an object. The inventions process uses the 701 effective ratios and 701 value added ratios as a baseline through these simulations, since each user's 600 athletic ability for different 300 motions is different. The process then uses the said user's 450 historical body's response to specific workouts and diets and formulates the perfect training regimen for that particular user. For example, the athletes 701 value added standard deviation for the right quad increases by 75% when under 600 fatigue. The process then 701 correlates previous workouts with the 600 reduction of fatigue. For example, the users' "Barbell Squat" is more statistical significant than the "Leg Press" when creating muscle hypertrophy for the purpose of reducing fatigue with respect to the optimal motion. The process finally couples the squat with a series of workouts that compliment it for the best possible results.

This process can also be used to learn how to lose fat mass or gain muscle mass independent of the 708 specific ergonomic of sports endeavor. The body fat mass is 300 collected through the signal distortion levels of the 201 SEMG, or consumer entered values of body fat mass for each body part. The inventions process for losing body fat mass and optimizing a diet is similar to the process stated above. One difference in this process is the simulation of the 805 trajectory is unnecessary. This process also differs by tailoring the 600 analytics directly to body fat mass, instead of the 708 optimal motion.

The optimal diet is a list of food categories that gives the user the desired amount of nutritional values for achieving the desired goal. If the goal is simply fat mass, or weight, reduction the optimal diet will produce a list of food items to achieve this weight loss, with respect to the amount of activity the user achieves. The list can be general, or it can be meal specific. It can, for example, produce a specific meal plan for the user when considering breakfast, lunch and dinner. It can also be set based on a prepared "training table" diet. The 900 display can also be set based on eating out and based on specific types of food genre. Because the process 300 collects data during specific activity related training, strength, and endurance related workouts, the diet can be updated after 450 every workout. It can also be updated to remain optimal in the long run every time the user eats. It also offers recommendations for the user, given their previous food preferences and required nutrition. If the user over eats the program will automatically provide information about how to compensate for the added nutrition during the next work-out or meal.

The 900 visual altering process also uses the combination of 450 data from the optimal workout and optimal diet. This is the process where the user can 900 visually view their simulated change in body mass that will occur in the future, briefly mentioned above. The invention simulates how the body will 900 visually change in the future, if the workout program and diet are followed. For example, if the 700 desired goal of the user is to lose 30 pounds in a year, the proper workout and diet regime is produced. The 900 visual altering process allows the user to see how their body will change at any time in the future. They can run the simulation for 1 month, 5 months, 9 months, or even their 'end product' at the end of the year. The process is completed by the estimated effects of the workout and diet plan. More specifically the delta, or change, of muscle hypertrophy and the delta, or change, in fat mass. To collect the delta fat mass at any particular time in the future, it compares the delta calories of the workout and diet. To collect the delta muscle mass, the process uses a statistical model that predicts muscle fiber increase given 450 historical data. The process uses the common knowledge of the exact amount of liters in each pound of fat mass and pound of muscle mass to 900 visually show the user's body changes in the future. This process continues to 1001 update when a change in workout or diet occurs.

The process also allows the user to determine the best possible equipment for their tailored game. To simulate which equipment is best for the end user, the invention allows the 802 sports equipment constants, to become a variable. The process then maximizes the sports 802 equipment variables to produce the best 805 end results, with respect to the users' 708 optimal motion. Once the 802 values are maximized, it then searches a list of sports equipment that are similar to the maximized 802 sports specific variables. For example, for a golfer, the such maximized 802 sport specific variables considered include, but is not limited to, the club head mass, the shaft stiffness, the shaft length, the golf ball, and other variables. It also runs analytics on such variables including the club head speed and the club head lead lag given the users motion.

Another variation is using 450 archived data for the purpose of coaching another individual through an 900 avatar. This process allows one user to 300 complete a trick, athletic motion, ergonomic motion, training regimen, or such and 450 archive the data. That 450 data is then 900 display on another users 203 preferred method to be recreated. The 450 data is 900 displayed the same way as an 708 optimal motion is 900 display. The difference is the data is collected from the 450 archive and not through the 708 optimal motion 705 process. The final end user can attempt to 300 recreate the motion and one of three biofeedback variations will 900 display 600 inconsistency from the initial user and the end users motion.

Another variation is using the 450 archived data to program a robotics unit. This variation uses 450 data collected from individuals, who agree to participate in the process, to program a 300 specific ergonomic motion to a robotics unit. Similar to the 900 display of an 708 optimal motion, a 300 motion that has been 705 optimized is 450 archived. This includes the exact 300 IMU values and 600 all analytics retaining to the motion. These 600 analytics include, but are not limited to, the amount of force throughout the motion, the amount of angular acceleration throughout the motion, and the amount of velocity throughout the motion of each body part. Instead of 900 displaying all this 600 data into an avatar, as explained above, the 600 analyzed data is sent to a robotics unit to be 300 recreated. The robotics unit will process the data and replicate the 708 optimal motion according to the data. This process is using "donated" 300 ergonomic motions for the purpose of teaching a robotics unit the 300 exact X,Y,Z at time t for each body part, the 300 equivalent of the exact muscle flex (the amount of grip or pressure applied throughout the motion), and all 600 analytics pertaining to. Depending on the way the robot operates, these steps could include given direct instructions to the robotics actuator, or such.

In other variations of the 200 biometric system, respiration sensors, galvanic skin response sensors, temperature sensors, global positioning system sensors, vibration sensors, bio impedance sensors, bend-angle measurement sensors, and any other sensors relevant for the 300 data collection process. Another variation of the 200 biometric system includes added any of the previous listed sensors to a user's 802 equipment coupled with the 100 garment.

Another variation of the 1001 machine learning process is to calibrate the 202 IMU sensors. This variation uses the said motion key to 1001 calibrate the 202 IMU's when attached to the garment. This motion key is customizable to the user's preference, but a suggested motion key is given. For example, by touching the 202 IMUs on the right arm and chest in a sequence, the left arm's 202 IMUs will use the said 1001 machine learning process to calibrate for any deviations at all. The 201 sEMG values of the left arm will confirm the exact time when the user touches the location for the 1001 calibration process.

Once any 300 data is collected, the data is 400 stored and 450 archived. This data includes all 200 biometric sensors in use during every motion. It also includes the any relevant analytics through any of the inventions process', including the 500 data mining, 600 data session, 708 optimal motion, 805 trajectory analysis, 900 graphical user interface, 950 system clients, and 1001 machine learning.

300 Information collected and 600 analyzed through the inventions process may be 450 archived. The 450 archival storage system may be in contact with the 203 preferred device or may be 450 archived on the 203 preferred device. The 450 archived data can be retrieved for 500 data mining, 600 data sessions, research, nuero economics, 802 equipment modification, programming a robotics unit, or such, but only under the direct consent of the said user.

The present invention is well adapted to carry out the objectives and attain both the ends and the advantages mentioned, as well as other benefits inherent therein. While the present invention has been depicted, described, and is defined by reference to particular embodiments of the invention, such reference does not imply a limitation to the invention, and no such limitation is to be inferred. The depicted and described embodiments of the invention are exemplary only, and are not exhaustive of the scope of the invention. Consequently, the present invention is intended to be limited only be the spirit and scope of the claims, giving full cognizance to equivalents in all respects.

I claim:

1. An apparatus for simulating a sports activity to predict a future trajectory of a sports object related to the sports activity, the apparatus comprising:

a clothing top with a multiplicity of physiological sensors embedded therein and at least one microcontroller connecting port attached to the multiplicity of physiological sensors;

a clothing bottom with a multiplicity of physiological sensors embedded therein and a at least one microcontroller connecting port attached to the multiplicity of physiological sensors;

a micro controller unit (MCU) electronically connected to the clothing microcontroller connecting ports, said MCU including memory, an inertial measurement unit (IMU), and digital communication equipment;

wherein an athlete dons said clothing top and said clothing bottom and performs a sports activity and said MCU, said physiological sensors and said IMUs collect a stream of athlete movement data;

a network that collects said stream of athlete movement data, processes said stream of athlete movement data and computes the future trajectory of said sports object based on the said stream of athlete movement data provided by the physiological sensors and IMU;

a mobile device that connects digitally to the microcontroller and to the network with said digital communication equipment, said mobile device including software that transforms the data into an image to allow analysis of the sports activity;

and wherein said athlete performs a series of movements for said sports activity to create a series of sports activity motions (n, n+1, n+2 . . . where n is the sports activity motion), and wherein said network stores said stream of athlete movement data from each motion of said series of sports activity motions, and compares a subsequent sports activity motion n+1 with a previous sports activity motion n to analyze said athlete movement.

* * * * *